(12) United States Patent
Takahashi et al.

(10) Patent No.: US 7,875,108 B2
(45) Date of Patent: Jan. 25, 2011

(54) INACTIVATING DEVICE FOR VIRUS, BACTERIA, ETC. AND AIR CONDITIONER USING THE SAME

(75) Inventors: Kazuo Takahashi, Ota (JP); Hiroshi Noguchi, Ashikaga (JP); Hiroaki Usui, Ora-gun (JP); Tsuyoshi Rakuma, Ora-gun (JP); Tetsuya Yamamoto, Ota (JP)

(73) Assignee: Sanyo Electric Co., Ltd., Moriguchi-shi (JP)

( * ) Notice: Subject to any disclaimer, the term of this patent is extended or adjusted under 35 U.S.C. 154(b) by 1206 days.

(21) Appl. No.: 11/421,916

(22) Filed: Jun. 2, 2006

(65) Prior Publication Data
US 2006/0273470 A1 Dec. 7, 2006

(30) Foreign Application Priority Data

| Jun. 3, 2005 | (JP) | 2005-164081 |
| Jun. 29, 2005 | (JP) | 2005-190078 |
| Jun. 29, 2005 | (JP) | 2005-190079 |

(51) Int. Cl.
*A61L 2/02* (2006.01)
*A61L 9/00* (2006.01)

(52) U.S. Cl. .......... 96/227; 96/243; 96/244; 422/4; 422/123; 422/124; 422/28; 422/186.14; 422/186.15

(58) Field of Classification Search .......... 95/8, 95/10, 149; 96/223, 227, 243–244; 422/4, 422/120, 123–124, 186, 14, 186.15, 186.07, 422/186.08; 261/4
See application file for complete search history.

(56) References Cited

U.S. PATENT DOCUMENTS

| 4,663,091 | A | | 5/1987 | Seo et al. |
| 5,354,515 | A | | 10/1994 | Ushimaru et al. |
| 5,518,591 | A | * | 5/1996 | Pulliainen et al. .......... 205/782 |
| 5,858,201 | A | * | 1/1999 | Otsuka et al. .......... 205/701 |
| 5,944,978 | A | * | 8/1999 | Okazaki .......... 205/701 |
| 7,407,624 | B2 | * | 8/2008 | Cumberland et al. .......... 422/28 |
| 2003/0024828 | A1 | * | 2/2003 | Kondo et al. .......... 205/742 |
| 2004/0037737 | A1 | | 2/2004 | Marais et al. |
| 2004/0262241 | A1 | * | 12/2004 | Socha .......... 210/760 |

FOREIGN PATENT DOCUMENTS

| DE | 101 57 187 A1 | 6/2003 |
| EP | 0 792 584 A1 | 9/1997 |
| EP | 1 496 314 A1 | 1/2005 |
| JP | 2002-181358 | * 6/2002 |
| JP | 2002-181358 A | 6/2002 |

* cited by examiner

*Primary Examiner*—Duane Smith
*Assistant Examiner*—Ives Wu
(74) *Attorney, Agent, or Firm*—Westerman, Hattori, Daniels & Adrian, LLP

(57) ABSTRACT

An inactivating device for inactivating virus, bacteria, etc. including a humidifying unit for humidifying flowing air, a humidifying water supply unit for supplying the humidifying unit with humidifying water containing active oxygen species achieved by electrolyzing tap water, and a concentration adjusting unit for adjusting the concentration of the active oxygen species in the humidifying water to a predetermined concentration.

10 Claims, 11 Drawing Sheets

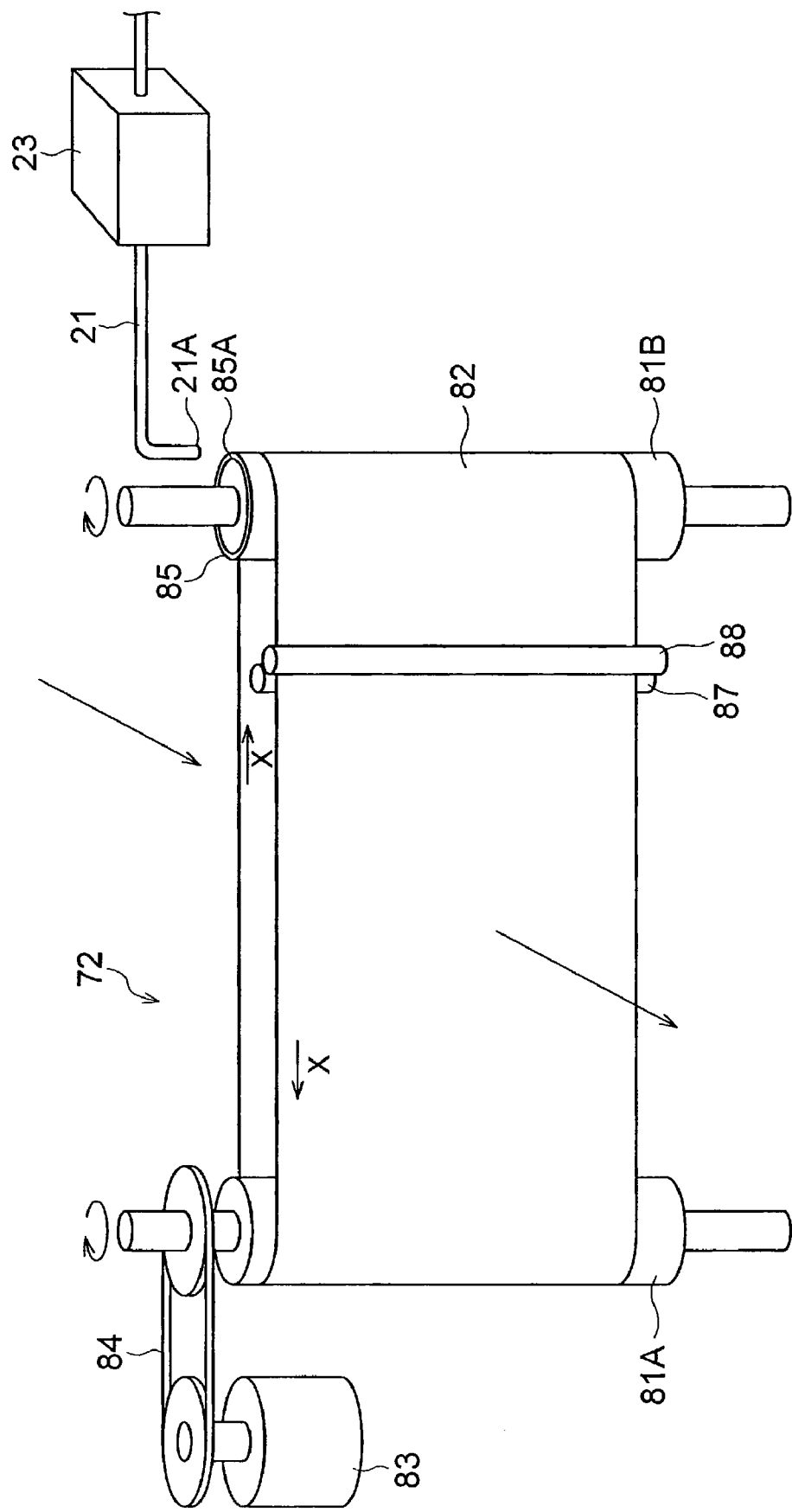

INACTIVATING DEVICE FOR VIRUS, BACTERIA, ETC. AND AIR CONDITIONER USING THE SAME

BACKGROUND OF THE INVENTION

1. Field of the Invention

The present invention relates to an inactivating device for humidifying flowing air while inactivating virus, bacteria, etc. contained in the air with humidifying water containing active oxygen specifies, and an air conditioner having the inactivating device.

2. Description of the Related Art

In general, there is known a humidifier in which tap water is adsorbed by a humidifying element and blow-out air is passed through the humidifying element to humidify the air with the water evaporated by the humidifying element. In this type of humidifier, repetitive wetting and drying causes the humidifying element to fall into a state where various bacteria is liable to breed, and thus there is a risk that bacteria, foul odor, fungus, etc. occurring in the humidifier may be blown out together with the blow-out air.

In order to solve this problem, for example, JP-A-2002-181358 has proposed an air conditioner having a humidifier in which hypochlorous acid (one kind of active oxygen specifies) is generated by using tap water and added to tap water to prevent breeding of various bacteria in the humidifying element.

By using this type of humidifier, it is possible to inactivate virus, bacteria or the like (hereinafter referred to as virus or the like) floated in the air. In this specification, the term of "inactivate virus, bacteria or the like" covers not only "sterilize or disinfect virus, bacteria or the like", but also "remove or filter virus, bacteria or the like". The concentration of active oxygen specifies for inactivating virus or the like is varied in accordance with the type of the virus or the like. On the other hand, the type of the target virus or the like to be inactivated is different in accordance with the place where a humidifier or an air conditioner is set up and the season under which these apparatuses are operated.

Accordingly, there is a problem that it is impossible to effectively inactivate virus or the like at some place where the humidifier or the air conditioner set up or under some season.

SUMMARY OF THE INVENTION

The present invention has been implemented in view of the foregoing situation, and has an object to provide an inactivating device that can effectively inactivate (sterilize, disinfect, remove, etc.) virus, bacteria, etc. without being affected by a place where a humidifier or an air conditioner is set up, a season under which the humidifier or the air conditioner is operated, and an air conditioner having the inactivating device.

In order to attain the above object, according to a first aspect of the present invention, there is provided an inactivating device for inactivating virus, bacteria, etc. that comprises a humidifying unit for humidifying flowing air; a humidifying water supply unit for supplying the humidifying unit with humidifying water containing active oxygen species achieved by electrolyzing tap water; and a concentration adjusting unit for adjusting the concentration of the active oxygen species in the humidifying water to a predetermined concentration.

In the inactivating device, the humidifying water supply unit is equipped with at least a pair of electrodes for generating the humidifying water, and the concentration adjusting unit changes the flow rate of tap water passing between the electrodes so that the concentration of the active oxygen species in the humidifying water is adjusted to the predetermined concentration.

In the inactivating device, the concentration adjusting unit is equipped with a flow rate adjusting valve for adjusting the flow rate of humidifying water in accordance with the concentration of chlorine ions of tap water.

In the inactivating device, the concentration adjusting unit is equipped with a flow rate adjusting valve for adjusting the flow rate of humidifying water in accordance with the conductivity of tap water.

In the inactivating device, the humidifying water supply unit is equipped with at least a pair of electrodes for generating the humidifying water, and the concentration adjusting means varies current flowing between the electrodes or a voltage applied between the electrodes so that the concentration of the active oxygen species in the humidifying water is adjusted to the predetermined concentration.

In the inactivating device, the concentration adjusting means varies the current flowing between the electrodes or the voltage applied between the electrodes in accordance with the concentration of chlorine ions in the tap water.

In the inactivating device, the humidifying water supply unit is equipped with at least a pair of electrodes for generating the humidifying water, and the concentration adjusting unit varies a time for current supply to the electrodes so that the concentration of the active oxygen species in the humidifying water is adjusted to the predetermined concentration.

In the inactivating device, the concentration adjusting unit varies the time for current supply to the electrodes in accordance with the concentration of chlorine ions of the tap water.

In the inactivating device, humidifying water supply unit comprises a stock tank for temporarily stocking the tap water and at least a pair of electrodes that are disposed in the stock tank and generate the humidifying water, and the concentration adjusting unit varies a stock time of the tap water in the stock tank so that the concentration of the active oxygen species in the humidifying water is adjusted to the predetermined concentration.

In the inactivating device, the concentration adjusting unit is equipped with an opening/closing valve whose opening/closing operation is controlled so that the stock time of the tap water in the stock tank is changed in accordance with the concentration of chlorine ions in the tap water.

In the inactivating device, the concentration adjusting unit is equipped with an opening/closing valve whose opening/closing operation is controlled so that the stock time of the tap water in the stock tank is changed in accordance with the conductivity of the tap water.

In the inactivating device, the humidifying water supply unit comprises a stock tank for temporarily stocking tap water, and at least a pair of electrodes that are disposed in the stock tank and generate humidifying water, and the concentration adjusting unit varies any one of current flowing between the electrodes, a voltage applied between the electrodes and a time for current supply to the electrodes so that the concentration of the active oxygen species in the humidifying water is adjusted to the predetermined concentration.

In the inactivating device, the humidifying unit is equipped with a holding unit for temporarily holding humidifying water having an inactivating action that is generated from tap water by supplying current to electrodes immersed in the tap water and then supplied to the humidifying unit when no air is supplied.

In the inactivating device, the holding unit is equipped with an opening/closing valve disposed at a water discharge port of the humidifying unit.

In the inactivating device, the humidifying unit is equipped with an endless filter that is suspended between a pair of rollers and rotated by rotation of the rollers, and the filter being supplied with the humidifying water having the inactivating action.

In the inactivating device, the filter comprises a positively-charged filter.

In the inactivating device, at least one of the rollers is provided with a water-holding member for temporarily holding the humidifying water having the inactivating action, and the humidifying water concerned is supplied to the filter through the water-holding member when the filter and the roller concerned coming into contact with each other.

In the inactivating device, a wringing roller for removing a part of the humidifying water held by the filter is disposed on a rotating passage of the filter.

In the inactivating device, the active species contain at least one of hypochlorous acid, ozone and hydrogen peroxide.

In the inactivating device, the polarities of the electrodes are inverted regularly (periodically) or irregularly under a predetermined condition.

According to a second aspect of the present invention, there is provided an air conditioner including an air blowing fan and a heat exchanger disposed at an air blow-out port side of the air blowing fan, characterized by further comprising a humidifier for humidifying air introduced through the heat exchanger, a humidifying water supply unit for electrolyzing tap water to generate humidifying water containing active oxygen species, and supplying the humidifying water to the humidifier, and a concentration adjusting unit for adjusting the concentration of the active oxygen species in the humidifying water so that the concentration of the active oxygen species is equal to a predetermined concentration.

In the air conditioner, the humidifying water supply unit is equipped with at least a pair of electrodes for generating the humidity water, and the concentration adjusting unit changes at least one of the flow rate of tap water flowing between the electrodes, current flowing between the electrodes, a voltage applied between the electrodes and a time for current supply to the electrodes so that the concentration of the active oxygen species in the humidifying water is adjusted to the predetermined concentration.

In the air conditioner, the humidifying water supply unit is equipped with a stock tank for temporarily stocking tap water, and at least a pair of electrodes that are disposed in the stock tank and generate humidifying water, and the concentration adjusting unit changes any one of current flowing between the electrodes, a voltage applied between the electrodes and a time for current supply to the electrodes so that the concentration of the active oxygen species in the humidifying water is adjusted to the predetermined concentration.

The air conditioner further comprises an inactivating control unit for supplying the humidifying water containing the active oxygen species to the humidifier during a period when an air conditioning operation of the air conditioner is stopped, thereby inactivating viruses, etc. in the humidifier.

In the air conditioner, during the period when the air conditioning operation of the air conditioner is stopped, the humidifying water is supplied to the humidifier every predetermined time.

In the air conditioner, the humidifier is equipped with an endless filter that is suspended between a pair of rollers and moved by rotation of the rollers, and the humidifying water containing the active oxygen specifies is supplied to the filter.

BRIEF DESCRIPTION OF THE DRAWINGS

FIG. 11 is a perspective view showing the construction of a capture portion.

DETAILED DESCRIPTION OF THE PREFERRED EMBODIMENTS

Preferred embodiments according to the present invention will be described hereunder with reference to the accompanying drawings.

First Embodiment

Figure 1:
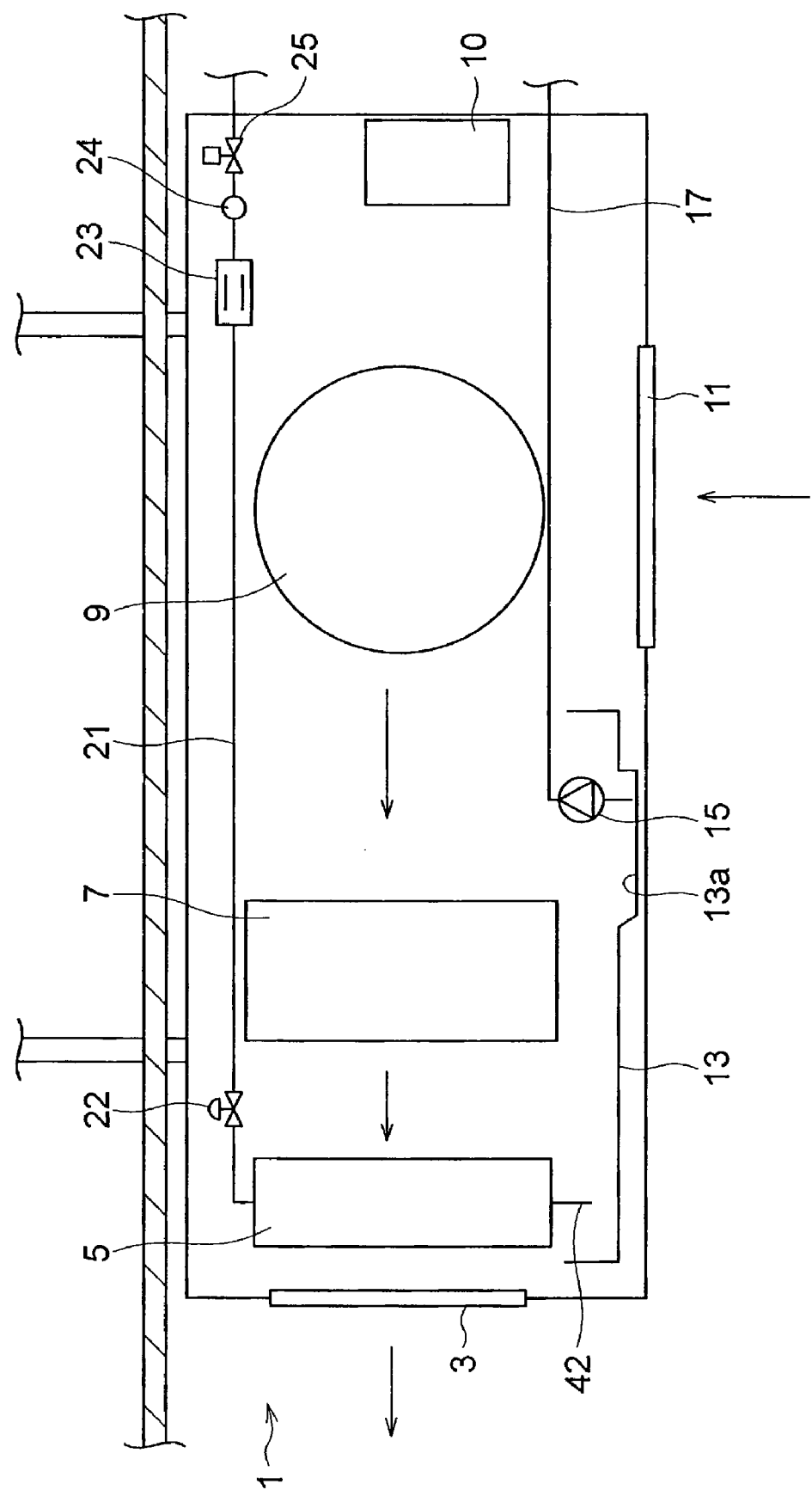
FIG. 1 is a diagram showing an embodiment of a ceiling-suspended type air conditioner according to the present invention.

In FIG. 1, reference numeral 1 represents the main body of an air conditioner (hereinafter referred to as the air conditioner main body), and the air conditioner 1 is hooked to suspending bolts suspended from the ceiling to be fixedly mounted below an indoor ceiling plate.

An air blow-out port 3 is formed at the front side of the air conditioner main body 1, and a humidifier 5, a heat exchanger 7 and an air blowing fan 9 are accommodated in this order from the air-blow-out port 3 side in the air conditioner main body 1 concerned. A suction port 11 is formed below the air blowing fan 9 at the bottom surface of the air conditioner main body 1, and air sucked into the air conditioner main body 1 through the suction port 11 is blown out from the blow-out port 3 through the heat exchanger 7 and the humidifier 5 into the room by driving the air blow-out fan 9.

The heat exchanger 7 is a fin tube type heat exchanger. A refrigerant pipe (not shown) is connected to the heat exchanger 7, and the refrigerant pipe is led to the outside of the air conditioner main body 1, and connected to a compressor, a pressure-reducing device, an outdoor heat exchanger, etc. (not shown). Furthermore, a drain pan 13 formed of foam polystyrene for receiving drain water, etc. occurring in the heat exchanger and the humidifier 5. This drain pan 13 has a drain pool 13a whose bottom surface is formed to be lower in height by one step, and a drain pump 15 is disposed in the drain pool 13a. A drain hose 17 for discharging the drain water to the outside of the air conditioner main body 1 is connected to the drain port of the drain pump 15.

The humidifier 5 is connected to a water supply pipe 21 for supplying humidifying water to the humidifier 5, and the water supply pipe 21 is successively connected to a flow rate adjusting valve (concentration adjusting unit) 22 for adjusting the flow rate (amount) of the humidifying water to be supplied to the humidifier 5, an electrolytic unit (humidifying water supply unit) 23 for generating humidifying water having inactivating action from tap water, a conductivity meter 24 for detecting the conductivity of tap water, and an opening/closing valve 25 for supplying tap water to the electrolytic unit 23 in this order. In this specification, the term "tap water" is used in a broad sense, and it may contain running water, city water, etc. In short, any water may be covered by the tap water insofar as it contains or possibly generates active oxygen specifies.

The flow rate adjusting valve 22, the electrolytic unit 23, the conductivity meter 24 and the opening/closing valve 25 are connected to a controller 10 as a concentration adjusting control unit for concentratively controlling the air conditioner main body 1.

In this embodiment, the humidifier 5, the flow rate adjusting valve 22 and the electrolytic unit 23 constitute an inactivating device for inactivating virus, bacteria, etc.

Figure 2:
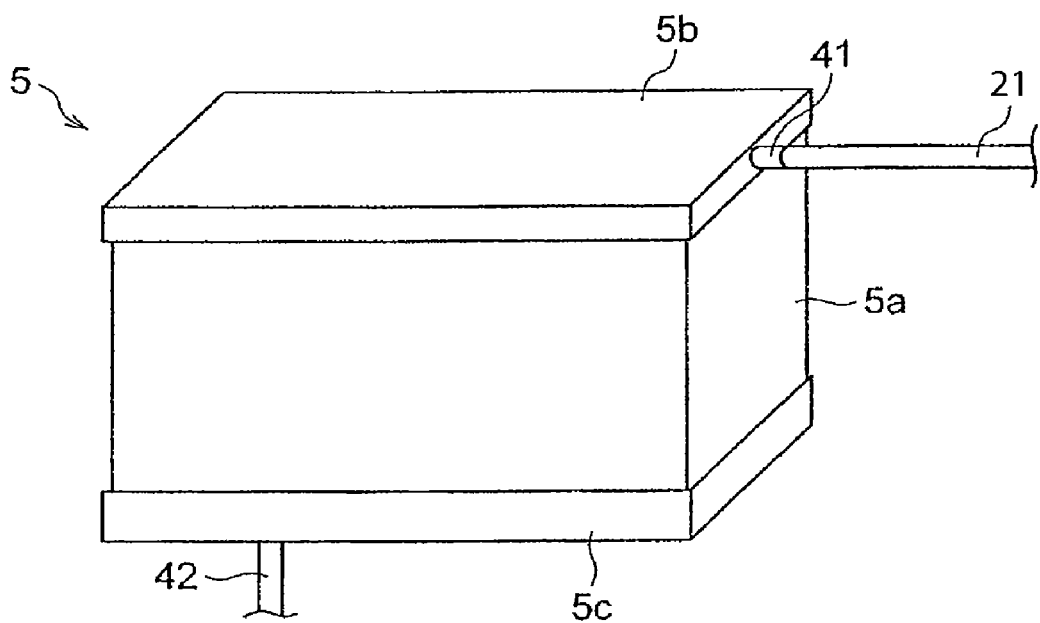
FIG. 2 is a perspective view showing the construction of a humidifier.

As shown in FIG. 2, the humidifier 5 is equipped with a humidifying element 5a having high water-holding capacity, a dispersing portion 5b that is disposed at the upper side of the humidifying element 5a and supplies humidifying water onto the upper surface of the humidifying element 5a while substantially uniformly dispersing the humidifying water, and a water receiving tray 5c that is disposed at the lower side of the humidifying element 5a and receiving humidifying water passing through the humidifying element 5a. The humidifying element 5a comprises non-woven fabric formed by acrylic fiber, polyester fiber or the like. The dispersing portion 5b has a connection port 41 which is connected to the water supply pipe 21 in one side surface thereof, and has many holes (not shown) formed in the bottom surface through which humidifying water supplied through the water supply pipe 21 is dispersed to the humidifying element 5a.

Furthermore, the water receiving tray 5c holds the humidifying element 5a from the lower side, and also receives humidifying water passing through the humidifying element 5a. A drain pipe 42 for guiding humidifying water to a drain pan 13 (see FIG. 1) is connected to the bottom surface of the water receiving tray 5c.

Figure 3:
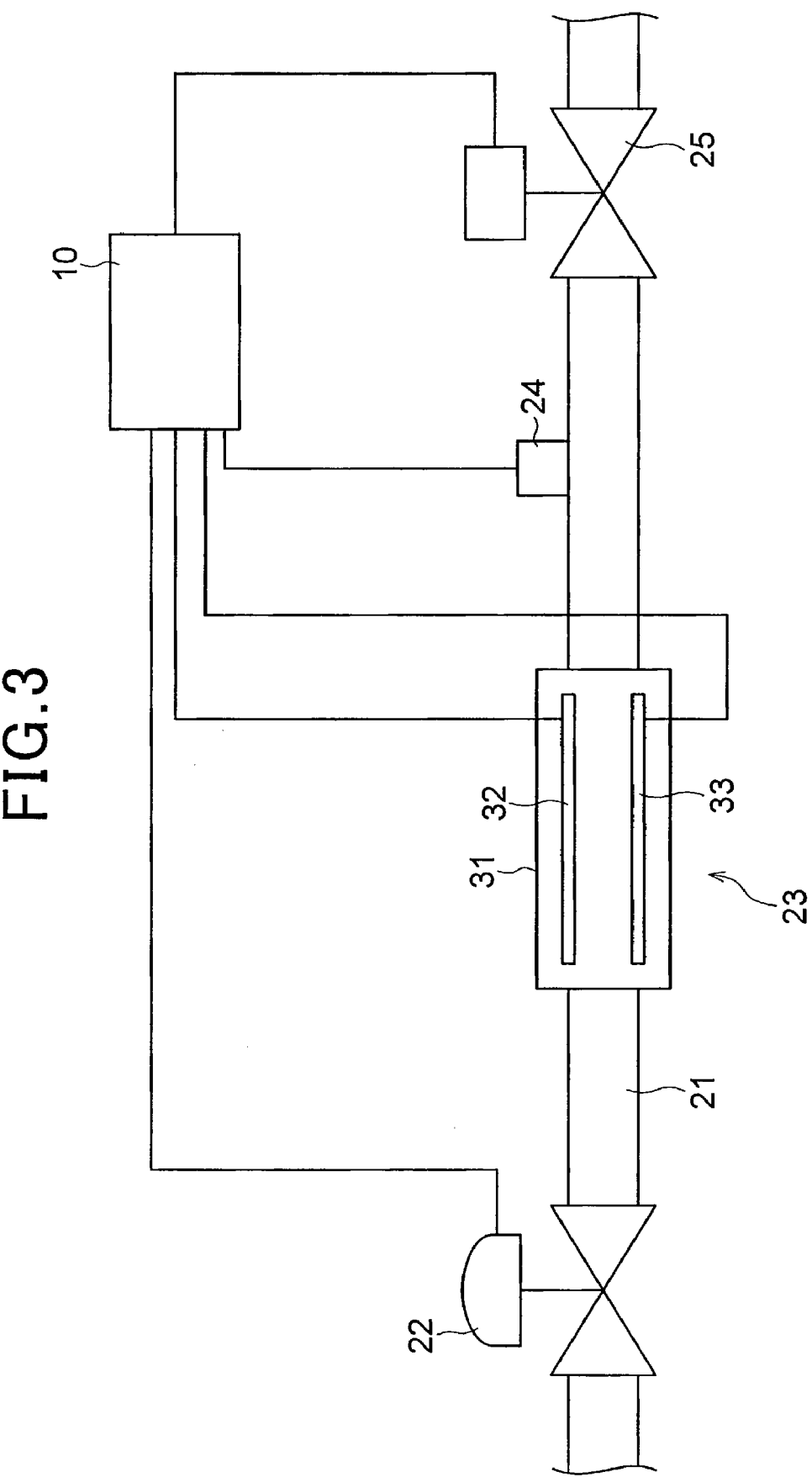
FIG. 3 is a diagram showing the construction of a concentration adjusting unit for humidifying water.
Figure 4:
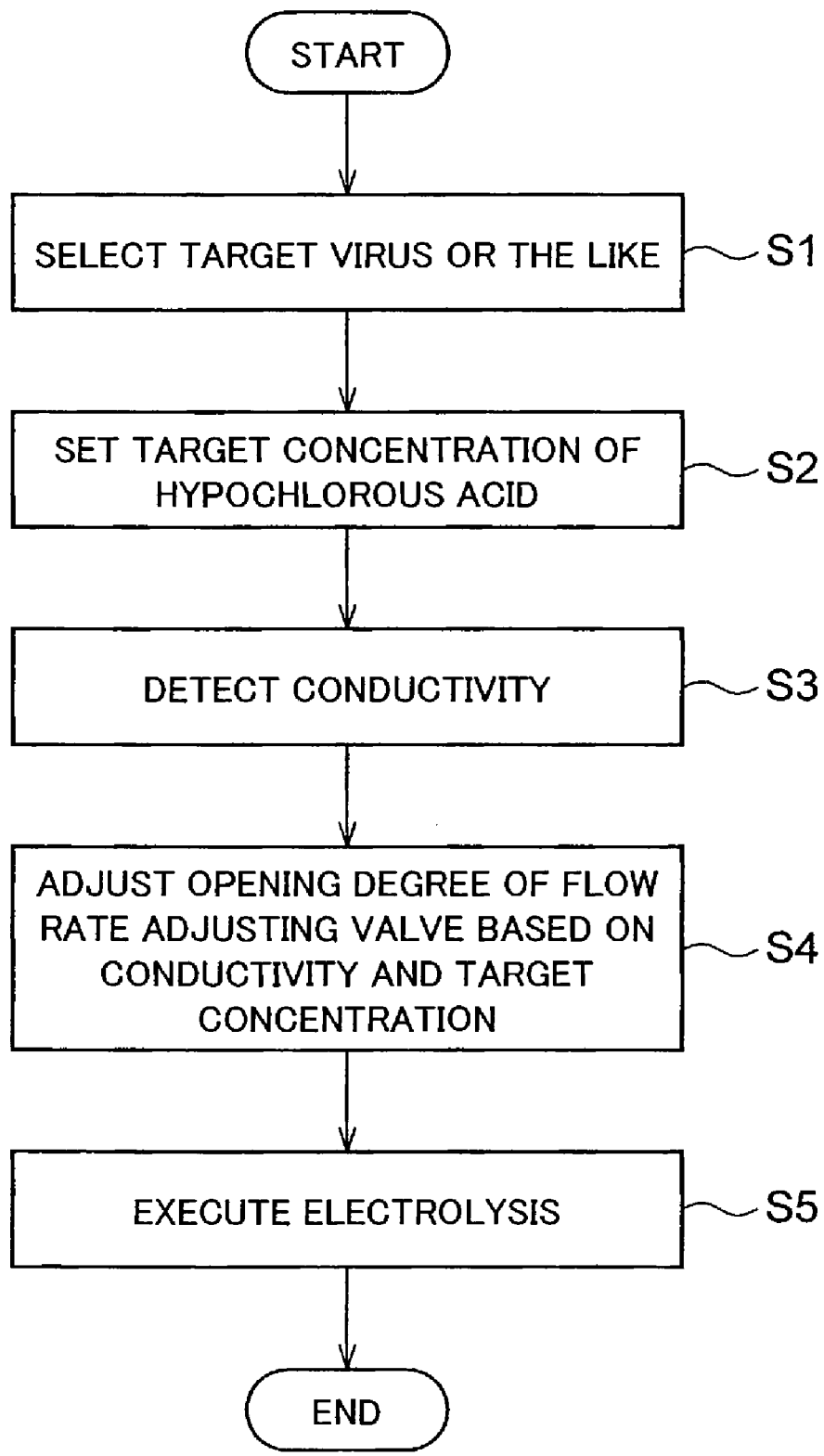
FIG. 4 is a flowchart showing a concentration adjusting operation.
Figure 5:
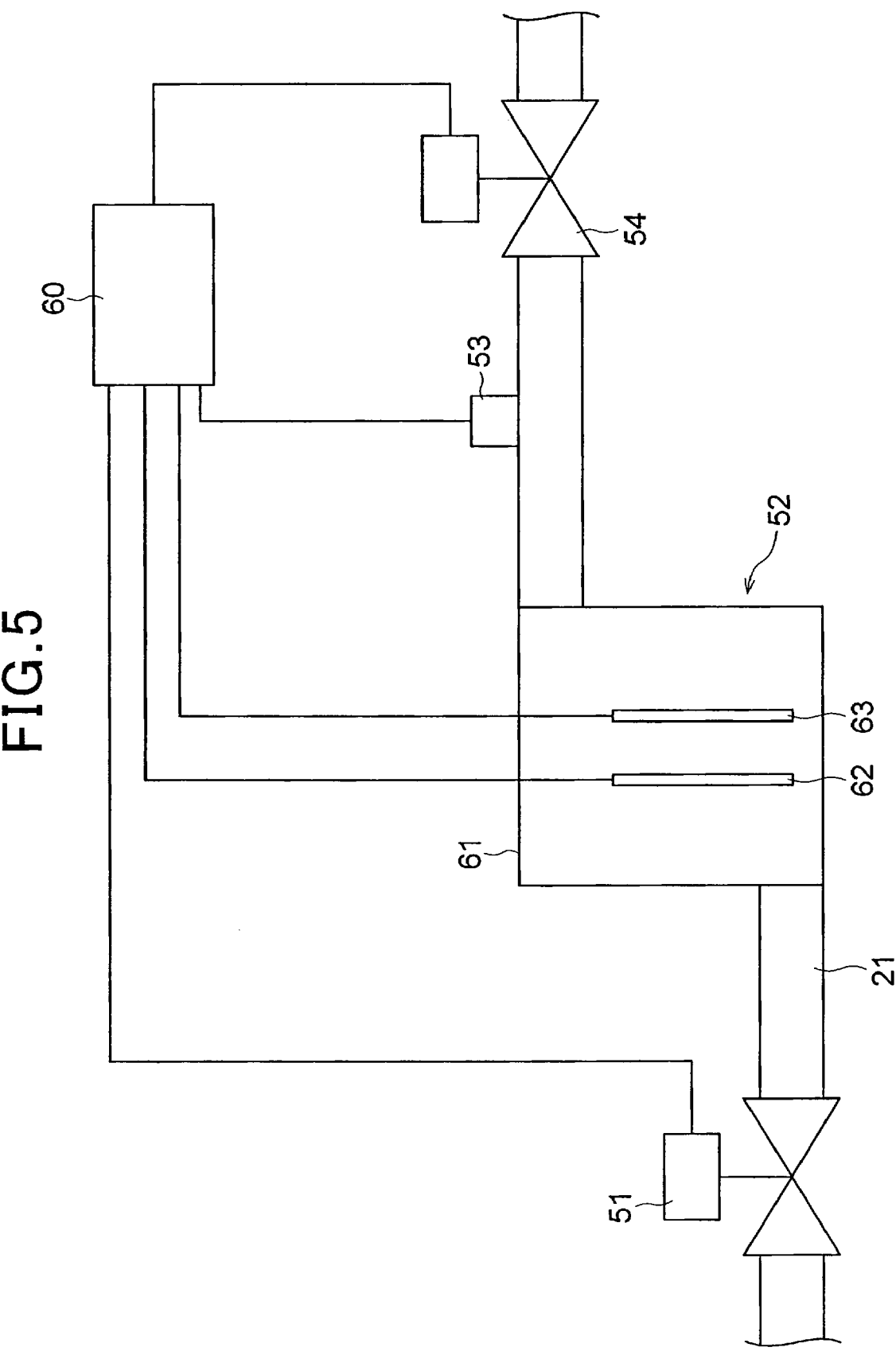
FIG. 5 is a diagram showing the construction of the concentration adjusting unit according to a second embodiment.
Figure 6:
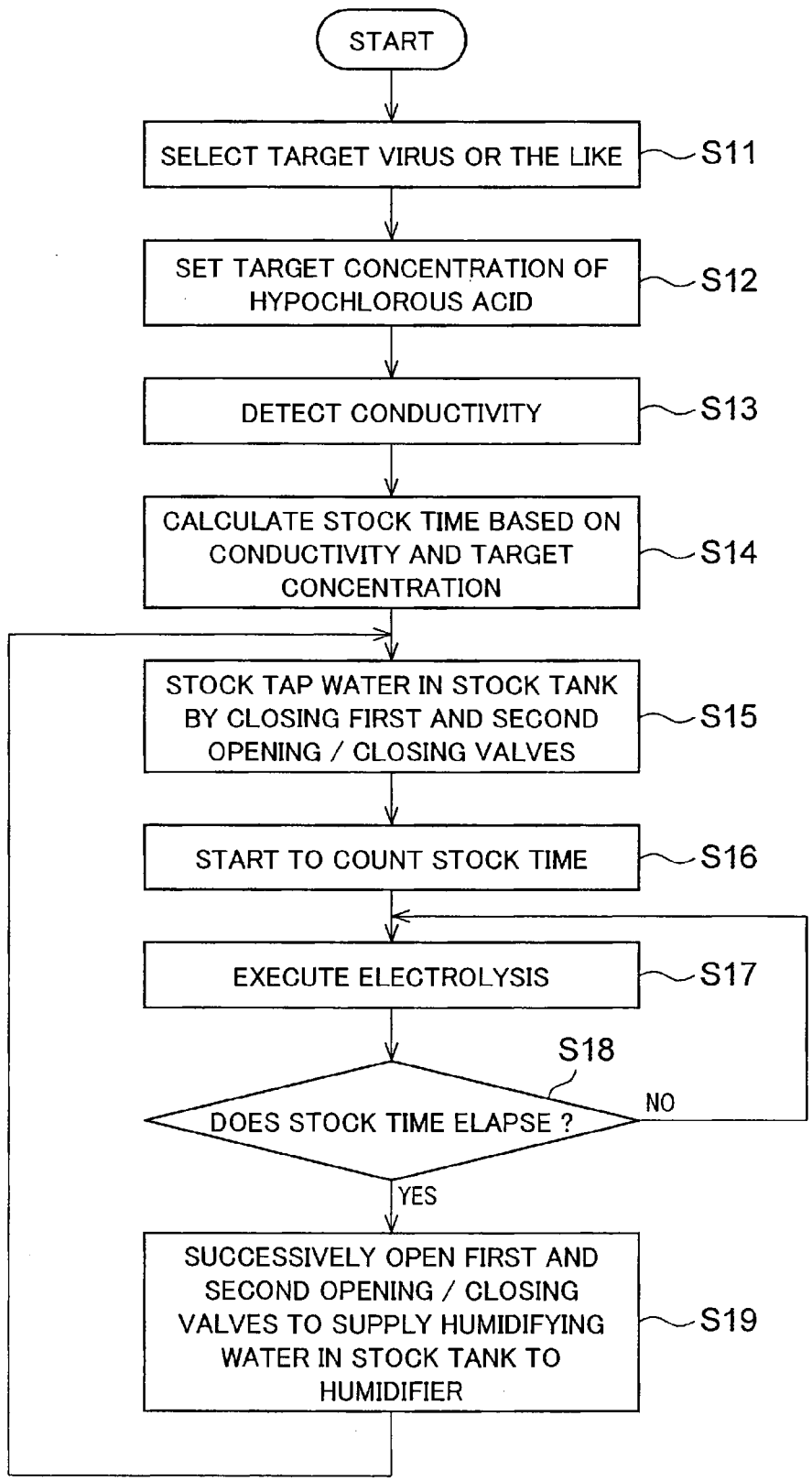
FIG. 6 is a flowchart showing the concentration adjusting operation according to the second embodiment.

As shown in FIG. 3, the electrolytic unit 23 is equipped with an electrolytic tank 31 having a larger diameter than the water supply pipe 21, and a pair of electrodes 32 and 33 disposed in the electrolytic tank 31. When current is supplied to the electrodes 32 and 33, the electrodes 32 and 33 electrolyze tap water flowing into the electrolytic tank 31 to generate active oxygen specifies.

Here, the active oxygen species means molecules having higher oxidation activation than normal oxygen and related substance thereof. For example, they may contain not only so-called strictly active oxygen such as super oxide anion, singlet oxygen, hydroxyl radical or hydrogen peroxide, but also so-called broad active oxygen such as ozone, hypohalogenous acid or the like.

The electrodes 32 and 33 are two electrode plates each of which comprises a base of Ti (titan) and a coating layer of Ir (iridium) and Pt (platinum), and a current value to be supplied to these electrodes 32 and 33 is set so that the current density is equal to a predetermined value (for example, 20 mA (milliampere)/cm² (square centimeter), and a predetermined free residual chlorine concentration (for example, 1 mg (milligram)/l (liter) is generated.

Described in detail, when current is supplied to tap water by the electrodes 32 and 33, the following reaction occurs at a cathode electrode:

$$4H^+ + 4e^- + (4OH^-) \rightarrow 2H_2 + (4OH^-)$$

Furthermore, the following reaction occurs at an anode electrode:

$$2H_2O \rightarrow 4H^+ + O_2 + 4e^-$$

At the same time, chlorine ion (added to tap water in advance) induces the following reaction:

$$2Cl^- \rightarrow Cl_2 + 2e^-$$

Furthermore, $Cl_2$ reacts with water as follows:

$$Cl_2 + H_2O \rightarrow HClO + HCl$$

In this construction, by supplying current to the electrodes 32 and 33, HClO (hypochlorous acid) having high sterilizing power is generated, and air is passed through the humidifying element 5a to which humidifying water containing hypochlorous acid is supplied, whereby various bacteria can be prevented from breeding in the humidifying element 5a and also virus floated in the air passing through the humidifying element 5a can be inactivated.

Furthermore, foul odor reacts with hypochlorous acid in the humidifying water when it passes through the humidifying element 5a, and thus it is ionized and dissolved in the humidifying water, so that the foul odor is removed from the air and thus the odor can be removed.

The flow rate adjusting valve 22 changes the flow rate (flow amount) of the humidifying water supplied to the humidifier 5 by adjusting the opening degree of the flow rate adjusting valve 22. In this embodiment, by adjusting the opening degree of the flow rate adjusting valve 22, the concentration of hypochlorous acid in the humidifying water can be changed to a predetermined value (for example, 1 to 20 mg/l). Specifically, when the opening degree of the flow rate adjusting valve 22 is adjusted so as to be closed, the flow rate of tape water flowing between the electrodes 32 and 33 of the electrolytic unit 23 is reduced. Since the current value supplied to the electrodes 32 and 33 is fixed irrespective of the flow rate of the tap water, and thus the amount of current flowing in tap water per unit volume is increased. Therefore, the electrolytic reaction at each of the electrodes 32 and 33 is promoted, whereby the concentration of hypochlorous acid thus generated can be increased.

Conversely, when the opening degree of the flow rate adjusting valve 22 is adjusted so as to be opened, the flow rate (amount) of tap water flowing between the electrodes 32 and 33 of the electrolytic unit 23 is increased, and thus the concentration of hypochlorous acid thus generated is reduced.

By changing the concentration of hypochlorous acid as described above, virus or the like as an inactivation target (virus or the like which is most strongly required to be inactivated) can be changed. In this embodiment, table data in which virus or the like as the inactivation targets are associated with the concentration of hypochlorous acid which is proper to inactivation of virus or the like is stored in a memory (not shown) of the controller 10.

An indoor remote controller (not shown) for operating the air conditioner main body 1 is connected to the controller 10, and when an indication of virus or the like to be inactivated is input through the indoor remote controller, the controller 10 sets the concentration of hypochlorous acid corresponding to the indication to a target concentration.

The operation of the controller 10 will be described hereunder.

When an inactivation target (virus or the like) is selected through the indoor remote controller by a user (step S1), the controller 10 sets to a target concentration the concentration of hypochlorous acid proper to inactivate the target virus or the like thus selected (step S2). Here, the target concentration is normally set to a concentration at which many viruses, etc. (for example, mold fungus) existing at a setup place of the air conditioner main body 1 (for example, school). However, for example, when target virus which may rapidly increase in some season such as influenza virus or the like is selected, the controller 10 reads out the concentration of hypochlorous acid corresponding to influenza virus from the memory, and sets the concentration of hypochlorous acid to the target concentration. Subsequently, the controller 10 detects the conductivity of tap water supplied to the electrolytic unit 23 by the conductivity meter 24 (step S3).

Subsequently, the controller 10 adjusts the opening degree of the flow rate adjusting valve 22 on the basis of the detected conductivity and the target concentration so that the concentration of hypochlorous acid in the humidifying water reaches the target concentration (step S4), and the electrolysis of tap water in the electrolytic unit 23 is executed (step S5). Here, the concentration of chlorine ion in the tap water supplied to the electrolytic unit 23 is not so greatly varied in many districts. Therefore, the concentration of chlorine ion in tap water is measured in advance before or after the electrolytic unit 23 is set up, and the conductivity corresponding to the concentration of chlorine ion thus measured is stored in the memory of the controller 10 in advance.

Furthermore, with respect to the deviation of the concentration of chlorine ion in tap water, the conductivity of tap water is detected by the conductivity meter 24, and the concentration of chlorine ion in tap water is calculated and corrected on the basis of the detection value. According to this method, it can be calculated how degree the flow rate adjusting valve 22 is opened/closed (i.e., the opening degree is determined) to generate humidifying water containing hypochlorous acid of the target concentration from tape water of a predetermined chlorine ion concentration.

In this construction, data for the relationship between the target concentration of hypochlorous acid and the valve opening degree are achieved by experiments, etc., and stored in the memory of the controller 10 every conductivity. Therefore, by adjusting the valve opening degree of the flow rate adjusting valve 22 to a predetermined opening degree in accordance with the detected conductivity, the concentration of hypochlorous acid in humidifying water is adjusted to the target concentration to inactivate the target virus or the like.

Accordingly, the humidifying water containing hypochlorous acid of the target concentration corresponding to target virus is supplied to the humidifier 5, and air is passed through the humidifying element 5*a* of the humidifier 5, whereby the target virus floated in the air can be inactivated. In this construction, for example when influenza virus is selected, the humidifying water of hypochlorous acid having the concentration which is set to inactivate the influenza virus is supplied to the humidifying element 5*a*. Therefore, when influenza virus passes through the humidifying element 5*a*, the influenza virus concerned can be inactivated, and thus the contamination of influenza virus can be suppressed.

According to this embodiment, there are provided the humidifier 5 for humidifying flowing air, at least a pair of electrodes 32 and 33 that are disposed in the humidifier and generate humidifying water achieved by electrolyzing tap water, and the flow rate adjusting valve 22 for changing the flow rate of tap water passing between the electrodes 32 and 33 to adjust the concentration of hypochlorous acid in the humidifying water to a predetermined concentration. Therefore, the opening degree of the flow rate adjusting valve 22 is adjusted in accordance with the type of virus or the like, whereby humidifying water having hypochlorous acid having the concentration for inactivating the virus or the like.

According to this embodiment, the humidifying water containing hypochlorous acid having the concentration concerned is supplied to the humidifier 5, and air is passed through the humidifying element 5*a* of the humidifier 5, whereby the target virus or the like can be effectively inactivated. Furthermore, foul odor reacts with hypochlorous acid in the humidifying water when it passes through the humidifying element 5*a*, and it is ionized and dissolved in the humidifying water, so that the foul odor can be removed from the air and thus the odor can be removed.

Furthermore, according to this embodiment, the humidifying water containing hypochlorous acid is passed from the lower side of the humidifier 5 through the drain pipe 42 and then discharged to the drain pan 13. Therefore, the drain water stocked in the drain pan 13 is contaminated with the humidifying water, whereby occurrence of various bacteria in the drain water can be prevented by hypochlorous acid in the humidifying water and thus occurrence of slime on the drain pan 13 can be prevented. Therefore, the frequency of cleaning of the drain pan 13 and maintenance can be reduced, and thus the labor required for the cleaning and the maintenance can be reduced.

Still furthermore, according to this embodiment, the humidifier 5 is provided at the air blow-out port 3 side of the air conditioner main body 1, and thus the air blown out from the humidifier is prevented from being directly introduced to the heat exchanger 7. Therefore, even when air blown out from the humidifier 5 is contaminated with hypochlorous acid, the heat exchanger 7 can be prevented from being corroded by hypochlorous acid.

In this embodiment, in order to set the concentration of hypochlorous acid in the humidifying water to a predetermined concentration, the opening degree of the flow rate adjusting valve 22 is adjusted in accordance with the conductivity of tap water. However, for example when virus to be inactivated is specified and also the variation of the conductivity of tap water is little, the conductivity of tap water may be measured in advance when the air conditioner main body 1 is set up, thereby presetting the valve opening degree corresponding to the conductivity concerned and the target concentration of hypochlorous acid.

Furthermore, in this embodiment, when the electrolysis of tap water is started, the conductivity of tap water is detected. The conductivity of tap water is not greatly varied during a day, and thus the conductivity of tap water may be detected only once per several start times of the electrolysis of tap water without being detected every time.

Second Embodiment

In the first embodiment described above, by changing the flow rate of tap water passing between the electrodes 32 and 33, the concentration of hypochlorous acid in the humidifying water is adjusted to a predetermined concentration. According to the second embodiment, by changing a retention (stock) time of tap water in a stock tank, the concentration of hypochlorous acid in the humidifying water is adjusted to a predetermined concentration.

As shown in FIG. 5, the water supply pipe 21 connected to the humidifier 5 is successively connected to a first opening/ closing valve (concentration adjusting unit) for supplying humidifying water to the humidifier 5, an electrolytic unit 52 for generating humidifying water having inactivating action from tap water, a conductivity meter 54 for detecting the conductivity of tap water, and a second opening/closing valve 54 for supplying tap water to the electrolytic unit 52. The first opening/closing valve 51, the electrolytic unit 52, the conductivity meter 53 and the second opening/closing valve 54 are connected to a controller 60 as a concentration adjusting control unit.

The electrolytic unit 52 is equipped with a stock tank (electrolytic tank) 61 disposed in the supply pipe 21, and a pair of electrodes 62 and 63 disposed in the electrolytic tank 61. When current is supplied to the electrodes 62 and 63, tap water flowing into the stock tank 61 is electrolyzed to generate hypochlorous acid (active oxygen specifies). Here, the first opening/closing valve 51 is connected to the downstream side of the stock tank 61, and the second opening/closing valve 54 is connected to the upstream side of the stock tank 61.

Next, the operation of the controller 60 according to the second embodiment will be described.

Virus or the like as an inactivation target is selected from the indoor remote controller by a user (step S11). The controller 60 sets to a target concentration the concentration of hypochlorous acid proper to inactivation of the selected target virus or the like (step S12). Here, the target concentration is normally set to a concentration suitable for inactivate many viruses, etc. (for example, mold fungus) existing at a place where the air conditioner main body 1 is set up (for example, school). However, for example when a target virus having a risk that it is rapidly increased in some season like influenza virus is selected, the controller 60 reads out the concentration of hypochlorous acid corresponding to the target virus (influenza virus) from the memory, and sets the read-out concentration of the hypochlorous acid to the target concentration.

Subsequently, the controller 60 detects the conductivity of tap water supplied to the electrolytic unit 52 by the conductivity meter 53 (step S13). Subsequently, the controller 60 calculates, on the basis of the detected conductivity and the target concentration, the time (stock time or retention time) for which tap water is stocked in the stock tank 61 so that the concentration of hypochlorous acid in the humidifying water reaches the target concentration concerned (step S14). Here, the concentration of chlorine ion in tap water supplied to the electrolytic unit 52 is not greatly varied in many districts. Therefore, the concentration of chlorine ion in tap water is measured in advance before or after the electrolytic unit 52 is setup, and the conductivity corresponding to the concentration of chlorine ion thus measured is stored in the memory of the controller 60 in advance.

Furthermore, with respect to the deviation of the concentration of chlorine ion in tap water, the conductivity of tap water is detected by the conductivity meter 53, and the concentration of chlorine ion in tap water is calculated and corrected on the basis of the detection value. According to this method, there can be calculated a stock time for which the tap water is stocked in the stock tank 61 in order to generate humidifying water containing hypochlorous acid of the target concentration from tape water of a predetermined chlorine ion concentration.

In this construction, data for the relationship between the target concentration of hypochlorous acid and the valve opening degree are achieved by experiments, etc., and stored in a memory (not shown) of the controller 60 every conductivity. Therefore, by adjusting the stock time of the tap water in the stock tank 61 to a predetermined time in accordance with the detected conductivity, the concentration of hypochlorous acid in humidifying water is adjusted to the target concentration to inactivate the target virus or the like.

Subsequently, the controller 60 closes the first and second opening/closing valves 51 and 54 (step S15) to stock tap water in the stock tank 61, and the controller 60 starts the counting of the stock time T1 (step S16) and also executes the electrolysis (step S17). Subsequently, the controller 60 judges whether the stock time T1 has elapsed (step S18). If it is judged that the stock time T1 has not yet elapsed, the controller 60 continues to execute the electrolysis. On the other hand, if it is judged that the stock time T1 elapses, the controller 60 successively opens the first opening/closing valve 51 and the second opening/closing valve (step S19) to supply humidifying water containing hypochlorous acid of the target concentration to the humidifier 5, and the returns the processing to the step S15.

According to this process, the humidifying water having the target concentration of hypochlorous acid to the humidifier 5 and air is passed through the humidifying element 5*a* of the humidifier 5, whereby target virus floated in the air can be inactivated. In this construction, for example when influenza virus is selected, the humidifying water of hypochlorous acid whose concentration is proper to inactivate the influenza virus is supplied to the humidifying element 5*a*. Therefore, when influenza virus passes through the humidifying element 5*a*, the influenza virus concerned can be inactivated, and thus contamination of influenza virus can be suppressed. Furthermore, when foul odor passes through the humidifying element 5*a*, it reacts with hypochlorous acid in the humidifying water and it is ionized and dissolved in the humidifying water, so that the foul odor is removed from the air and thus the odor can be removed.

According to this embodiment, there are provided the humidifier 5 for humidifying flowing air, the stock tank 61 for temporarily stocking tap water to electrolyze the tap water and thus achieve humidifying water, at least a pair of electrodes 62 and 63 that are disposed in the stock tank 61 and generates humidifying water, and the first opening/closing valve 51 for changing the stock time of tap water in the stock tank 61 to thereby adjust the concentration of hypochlorous acid in the humidifying water to a predetermined concentration. Therefore, the humidifying water having hypochlorous acid whose concentration is suitable to inactivate the virus concerned, etc. by adjusting the stock time of tap water in the stock tank 61 in accordance with the type of virus or the like, for example.

According to this embodiment, the humidifying water having hypochlorous acid having the concentration concerned is supplied to the humidifier 5, and air is passed through the humidifying element 5*a* of the humidifier 5, whereby a target virus or the like can be effectively inactivated. Furthermore, when foul odor passes through the humidifying element 5*a*, it reacts with hypochlorous acid in the humidifying water, and thus it is ionized and dissolved in the humidifying water, so that the foul odor can be removed and thus the odor can be removed.

According to this embodiment, the humidifying water containing hypochlorous acid whose concentration is higher than that of the first embodiment can be created by setting the stock time of tap water stocked in the stock tank 61 to a sufficient time.

In the above-described embodiment, in order to adjust the concentration of hypochlorous acid in the humidifying water to a predetermined concentration, the flow rate of tap water passing between the electrodes 32 and 33 is changed, or the stock time of tap water stocked in the stock tank 61 in which the electrodes 62 and 63 are disposed is changed. However, the present invention is not limited to these embodiments. For example, by changing the value of current flowing in the electrodes or changing the voltage value applied between the electrodes, the concentration of hypochlorous acid in the humidifying water is adjusted to a predetermined concentration.

According to this construction, even when neither the flow rate adjusting valve 22 nor the first opening/closing valve 51 is disposed in the water supply pipe 21, the concentration of hypochlorous acid in the humidifying water can be changed to a high concentration by increasing the current flowing between the electrodes 32 and 33 (for example, 40 mA/cm$^2$ in current density). In this case, the concentration of hypochlorous acid in the humidifying water can be changed by merely using existing electrodes 32 and 33, so that the number of parts can be reduced, the cost can be reduced and the space can be saved. Furthermore, this construction may be combined with the construction of the first or second embodiment. According to this construction, humidifying water containing a high concentration of hypochlorous acid can be quickly generated.

Furthermore, by changing the current supply time to the electrodes, the concentration of hypochlorous acid in humidifying water may be adjusted to a predetermined concentration. According to this construction, for examples, the concentration of hypochlorous acid in humidifying water can be changed by a simpler construction that the construction in which the current value flowing between the electrodes 32 and 33 or the voltage value applied between the electrodes is changed. Furthermore, by combining this construction with the above-described embodiment, the current supply time to the electrodes can be reduced, and the life-time of the electrodes can be enhanced.

Third Embodiment

In general, the humidifier is used in a season having low humidity such as winter or the like, and it is not used in a season having relatively high humidity such as summer or the like. Accordingly, there is a risk that various bacteria breed in the humidifier in summer, and when bacteria, foul odor, fungus or the like occurs, they may be blown out together with blow-out air.

The third embodiment solves the above-described problem, and even in a season when no humidifier is used, the breeding of various bacteria in the humidifier can be suppressed.

Figure 7:
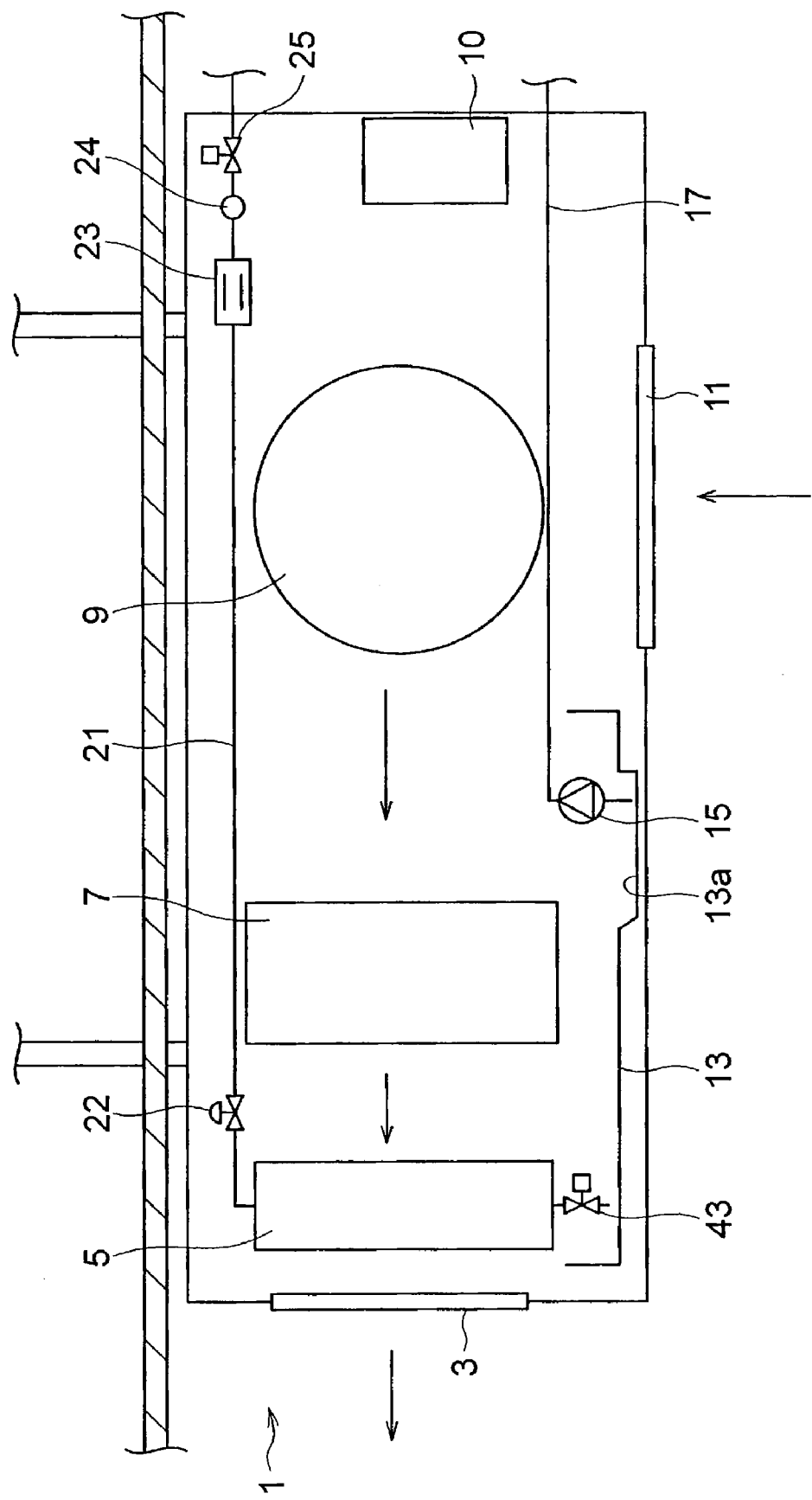
FIG. 7 is a diagram showing the main body of an air conditioner according to a third embodiment.
Figure 8:
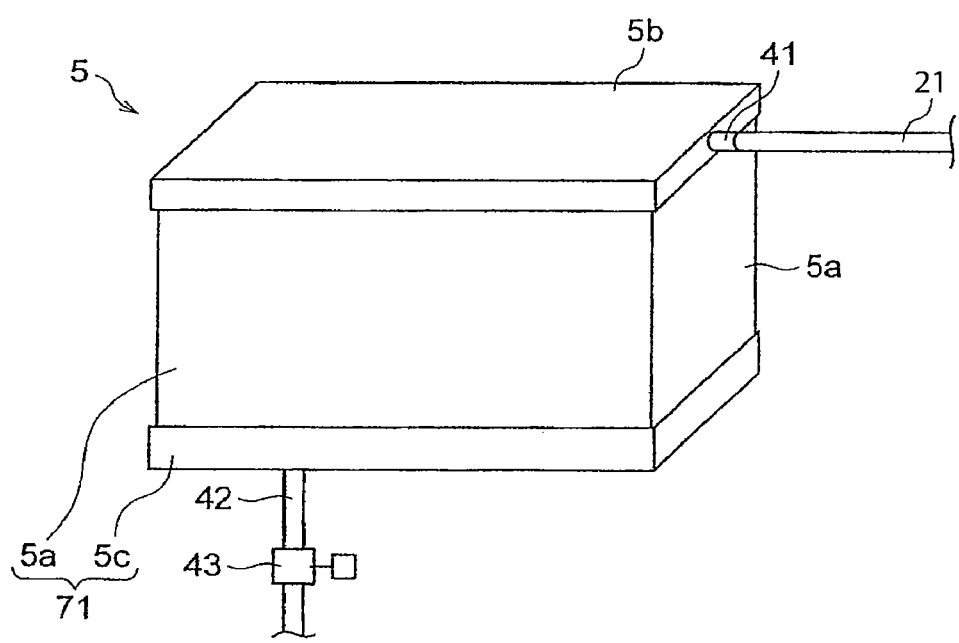
FIG. 8 is a perspective view showing a humidifier according to a third embodiment.
Figure 9:
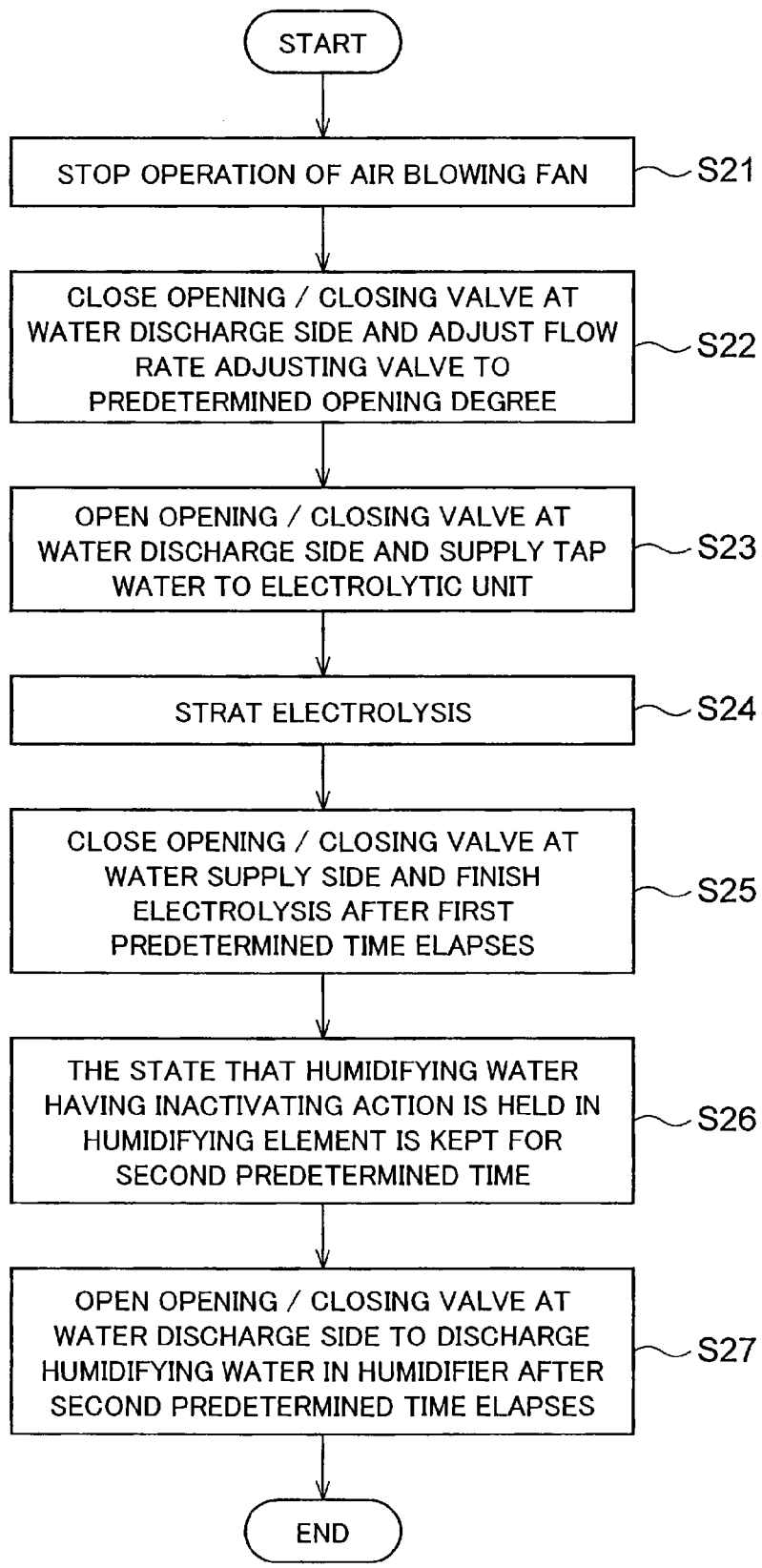
FIG. 9 is a flowchart showing the sterilization operation of the humidifier.

FIG. 7 is a diagram showing the air conditioner main body according to the third embodiment, and FIG. 8 is a perspective view showing the humidifier according to the third embodiment. The third embodiment is different from the construction shown in FIG. 1 in that the humidifier 5 is equipped with a holding unit for temporarily holding humidifying water. The same parts as shown in FIG. 1 are represented by the same reference numerals, and the description thereof is omitted.

As shown in FIG. 8, a water receiving tray 5c of the humidifier 5 supports the humidifying element 5a from the lower side and it can stock humidifying water passing through the humidifying element 5a. The drain pipe 42 for guiding humidifying water to the drain pan 13 (see FIG. 1) is connected to the bottom surface of the water receiving tray 5c, and an opening/closing valve 43 is secured to the drain pipe 42. In this construction, the humidifier 5 is equipped with the holding unit 71 for temporarily holding the humidifying water, and the holding unit 71 is equipped with the humidifying element 5a, the water receiving tray 5c and the opening/closing valve 43. The opening/closing valve 43 is connected to the controller 10 as a water holding controller, and the opening/closing valve 43 is closed under the control of the controller 10, whereby the humidifying water is stocked in the water receiving tray 5c. Therefore, even when the supply of the humidifying water is stopped, the lower portion of the humidifying element 5a is immersed with the humidifying water, and thus the humidifying water is sucked upwardly by the capillary phenomenon.

In this construction, by supplying current to the electrodes 32 and 33, HClO (hypochlorous acid) having strong sterilizing power occurs, and humidifying water containing hypochlorous acid, that is, humidifying water having an inactivating action (inactivating water) is supplied to the humidifier 5, whereby various bacteria can be prevented from occurring in the humidifying element 5a of the humidifier 5 and the humidifier 5 concerned.

In this construction, even in a season when the humidifier 5 is not operated (for example, summer season), humidifying water having the inactivating action is supplied into the humidifier 5 and held in the humidifying element 5a to execute the inactivating operation, thereby preventing breeding of various bacteria in the humidifying element 5a and the humidifier 5.

Next, the inactivating control operation in the humidifier 5 when the humidifier 5 is not used will be described in detail.

The inactivating control is executed by the controller 10 as the inactivating controller. This inactivating operation is executed when the air blowing fan 9 is stopped (for example, when the air conditioning operation is stopped (when no air is introduced). If the inactivating operation is executed during operation (for example, cooling operation) of the air blowing fan 9, the blown air would be humidified air.

When the operation of the air blowing fan 9 is stopped (step S21), the controller 10 closes the opening/closing valve 43 provided at the water discharge side of the humidifier 5, and also adjusts the flow rate adjusting valve 22 to a predetermined opening degree (step S22). In this case, by adjusting the opening degree of the flow rate adjusting valve 22 so that the valve is closed, the concentration of hypochlorous acid in the humidifying water can be increased (for example, 5 mg/l), and thus the inactivating time can be shortened. The data for the relationship between the opening degree of the flow rate adjusting valve 22 and the concentration of hypochlorous acid in the humidifying water generated by the electrolytic unit 23 are achieved by experiments, etc., and stored in a memory (not shown) of the controller 10.

In this construction, in order to shorten the inactivating time, the valve opening degree of the flow rate adjusting valve 22 is adjusted so as to increase the concentration of hypochlorous acid in the humidifying water. However, sterilization in the humidifier 5 can be sufficiently performed insofar as the sterilization time can be secured even when the concentration of hypochlorous acid is normal (for example, 1 mg/l).

Subsequently, the controller 10 opens the opening/closing valve 25 at the water supply side to supply tap water to the electrolytic unit 23 (step S23), and starts the electrolysis of tap water in the electrolytic unit 23 (step S24). The humidifying unit having the inactivating action that is generated by the electrolysis is supplied through the flow rate adjusting valve 22 to the humidifier 5. In this case, since the opening/closing valve 43 is closed, the supplied humidifying water is not discharged through the opening/closing valve 43. Accordingly, the humidifying water having the inactivating action is held in the water receiving tray 5c and the humidifying element 5a and carries out sterilization in the humidifying element 5a and the humidifier 5.

Subsequently, when a first predetermined time T1 elapses from the start of the supply of the humidifying water, the controller 10 closes the opening/closing valve 25 at the water supply side, and finishes the electrolysis (step S25). The first predetermined time T1 is set so that the humidifying water is prevented from being excessively supplied to the humidifier 5 by an amount larger than the permissible amount of the humidifying water which can be held in the water receiving tray 5c and the humidifying element 5a. In this construction, the supply amount per unit time is changed in accordance with the valve opening degree of the flow rate adjusting valve 22, and thus the first predetermined time T1 is set in accordance with the valve opening degree of the flow rate adjusting valve 22.

Subsequently, the state that the humidifying water is held in the water receiving tray 5c and the humidifying element 5a is kept for a second predetermined time T2 by the controller 10 (step S26). The second predetermined time T2 is set to such a sufficient value that the sterilization in the humidifier 5 is carried out by hypochlorous acid in the humidifying water. In this construction, the concentration of hypochlorous acid is changeable in accordance with the valve opening degree of the flow rate adjusting valve 22, and thus the second predetermined time T2 is set to the time corresponding the valve opening degree, that is, the concentration of hypochlorous acid.

Subsequently, when the second predetermined time T2 elapses, the controller 10 opens the opening/closing valve 43 to discharge the humidifying water in the humidifier (step S27), and then finishes the processing.

As described above, according to the above-described embodiment, there are provided the humidifier 5 for humidifying flowing air and the humidifying water supply unit for supplying humidifying water to the humidifier 5. The humidifying water supply unit is equipped with at least a pair of electrodes 32 and 33 for electrolyzing tap water by supplying current when no air is conducted and generating inactivating water containing hypochlorous acid, and the humidifier 5 is equipped with the holding unit 71 for temporarily holding the inactivating water which is generated by supplying current to the electrodes 32 and 33 and then supplied to the humidifier 5. Therefore, even during a period when the humidifier 5 is not used, hypochlorous acid is supplied to the humidifier 5 into the humidifier 5, whereby various bacteria can be prevented from breeding in the humidifier 5.

Furthermore, according to this embodiment, by adjusting the valve opening degree of the flow rate adjusting valve 22 to change the flow amount of tap water passing between the electrodes 32 and 33, the concentration of hypochlorous acid in the humidifying water having the inactivating action can be adjusted to a predetermined concentration. Therefore, the humidifying water containing a high concentration of hypochlorous acid can be supplied to the humidifier 5, and the inactivating time in the humidifier 5 can be shortened.

Still furthermore, according to this embodiment, the humidifying water containing hypochlorous acid is discharged from the lower side of the humidifier 5 to the drain pan 13. Therefore, the drain water stocked in the drain pan 13 is contaminated with the humidifying water, whereby occurrence of various bacteria in the drain water can be prevented, and thus occurrence of slime on the drain pan 13 can be prevented. Therefore, the cleaning and maintenance frequency of the drain pan 13 can be reduced, and thus the labor of the cleaning and maintenance can be reduced.

In the above-described embodiment, the concentration of hypochlorous acid in the humidifying water is adjusted to a predetermined concentration by changing the flow rate of tap water passing between the electrodes 32 and 33. However, the following construction may be adopted. That is, a stock tank (electrolytic tank) is disposed in the water supply pipe, a pair of electrodes are provided in the stock tank and a stock time of tap water stocked in the stock tank is changed, whereby the concentration of hypochlorous acid in the humidifying water is adjusted to a predetermined concentration.

Furthermore, in the above-described embodiment, the state that the humidifying water is held in the humidifying element 5a of the humidifier 5 is left for the second predetermined time T2, and after the second predetermined time elapses, the opening/closing valve 43 is opened to discharge the humidifying water. However, the present invention is not limited to this embodiment. For example, during the stop period of the air conditioning operation of the air conditioner 1, the opening/closing valve 43 is closed and inactivating water is supplied to the humidifier 5. Then, when the air conditioner 1 next starts the air conditioning operation, the opening/closing valve 43 is opened. Furthermore, during the stop period of the air conditioning operation of the air conditioner 1, the supply of the inactivating water to the humidifier 5 may be carried out every predetermined time.

Fourth Embodiment

Figure 10:
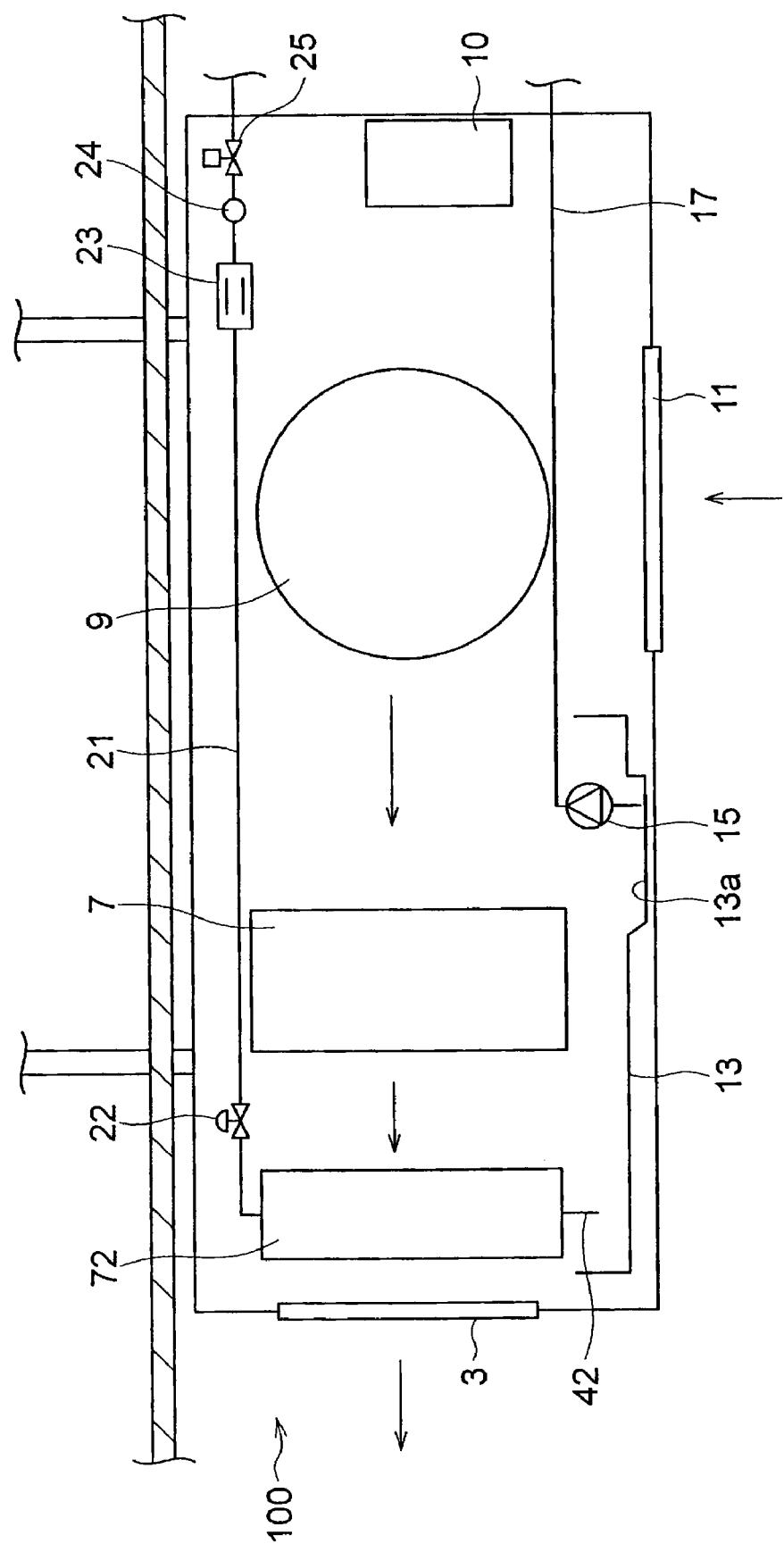
FIG. 10 is a diagram showing the main body of the air conditioner according to a fourth embodiment.

FIG. 10 is a diagram showing the air conditioner main body according to a fourth embodiment. In the air conditioner main body 100 according to the fourth embodiment, a capture portion 72 (humidifying unit) for capturing a virus or the like is provided in place of the humidifier 5 having the humidifying element. The capture portion 72 captures the virus or the like floated in the indoor air introduced through the air blowing fan 9, and discharges clean air to the room. The capture portion 72 is supplied with inactivating water having the inactivating action to inactivate the virus or the like captured by the capture portion 72.

As shown in FIG. 11, the capture portion 72 is equipped with a pair of rollers 81A and 81B, and a filter 82 suspended between the rollers 81A and 81B. This filter 82 is designed endlessly by connecting both the end portions of the filter 82 in the longitudinal direction to each other. In this construction, an electret filter whose surface is positively charged is used as the filter 82. It is generally known that viruses, etc. are negatively charged. Therefore, by using a positively charged electret filter, viruses, etc. can be easily captured.

A driving motor 83 for driving the roller 81A is connected to the roller 81A through a timing belt 84. When the driving motor 83 is driven, the roller 81A is rotated around the shaft thereof through the timing belt 84, and the filter 82 is rotated between the rollers 81A and 81B interlockingly with the rotation of the roller 81A. Furthermore, a water-holding member (water-holding unit) 85 for temporarily holding inactivating water is wound around the surface of the other roller 81. The water-holding member 85 is formed of non-woven fabric such as acrylic fiber, polyester fiber or the like, and a discharge port 21A of the inactivating water supply pipe 21 is disposed in the neighborhood of the upper end portion 85A of the water-holding member 85.

When the inactivating water drops to the upper end portion 85 of the water-holding member 85 through the discharge port 21A, the inactivating water diffuses from the upper end portion 85A of the water-holding member 85 downwardly, and infiltrates into the overall area of the water-holding member 85. When the driving motor 83 is continuously operated under the above state, the filter 82 is rotated between the rollers 81A and 81B. At this time, when the filter 82 and the water-holding member 85 of the roller 81B come into contact with each other, the inactivating water held by the water-holding member 85 infiltrates to the filter 82 in the width direction, so that the inactivating water is supplied to the filter 82. Accordingly, the inactivating water can be supplied to the overall filter 82, and the virus or the like captured by the filter 82 is inactivated by the inactivating water, and thus the clean air is supplied to the room.

Furthermore, a pair of wringing rollers 87 and 88 for wringing the inactivating water supplied to the filter 82 by pressing the filter 82 are provided at the downstream side of the roller 81B in the travel direction (in the direction of an arrow X in FIG. 11) of the filter 82. The wringing rollers 87 and 88 comprises a fixed roller 87 disposed inside the filter 82 and a movable roller 88 disposed so as to face the fixed roller 87 through the filter 82. The movable roller 88 is provided so that the distance thereof from the fixed roller 87 is freely variable. By changing the distance between the movable roller 88 and the fixed roller 87, the thickness of the filter being used or the amount of inactivating water to be wringed from the filter 82 can be changed.

According to this construction, by reducing the wringing degree of the filter 82, the amount of inactivating water contained in the filter 82 can be increased. Furthermore, by passing air of the air blowing fan 9 under the above state, indoor air can be also humidified.

In this construction, the rotational direction of each of the rollers 81A and 81B is determined so that the filter 82 passes over the roller 81B after the filter 82 captures the virus or the like. Therefore, the virus or the like thus captured can be immediately inactivated by the inactivating water, and thus the virus or the like can be prevented from scattering again while keeping their activation.

As described above, according to this embodiment, the inactivating device is equipped with the capture portion 72 for capturing virus, bacteria or the like in the flowing air, the capture portion 72 being equipped with the endless filter 82 which is suspended between the pair of rollers 81A and 81B and driven by rotating the rollers 81A and 81B, and also equipped with the electrolytic unit 23 for electrolyzing tap water to achieve inactivating water containing hypochlorous acid and supplying the inactivating water concerned to the filter 82. Therefore, the virus or the like captured by the filter 82 can be strongly inactivated by the inactivating water.

Furthermore, according to this embodiment, since the inactivating water is continued to be supplied to the filter 82, the inactivating function is not weakened with lapse of time, and the virus or the like captured by the filter 82 can be prevented from re-scattering with keeping their activation.

Still furthermore, according to this embodiment, the positively charged electret filter is used as the filter 82, and thus a negatively charged virus or the like is adsorbed by the positively charged electret filter, so that the virus or the like can be easily captured by the filter. In this embodiment, one roller 81B is provided with the water-holding member 85 for temporarily holding inactivating water, and the inactivating water is supplied to the filter 82 through the water-holding member 85 when the filter 82 and the roller 81B come into contact with each other. Therefore, the inactivating water can be supplied to the overall district of the filter 82 with a simple construction, and the virus or the like captured by the filter 82 can be inactivated.

Furthermore, in this embodiment, the wringing rollers 87 and 88 for removing a part of the inactivating water held in the filter 82 are disposed on the passage along which the filter 82 is moved. Accordingly, humidified air can be prevented from being discharged to the room by wringing the inactivating water from the filter 82 with the rollers 87 and 88. Furthermore, in this construction, the distance between the wringing rollers 87 and 88 is changeable, whereby a desired humid state can be realized even when the indoor air is humidified.

Still furthermore, according to this embodiment, the valve opening degree of the flow rate adjusting valve 22 is adjusted to change the flow rate (amount) of tap water passing between the electrodes 32 and 33, whereby the concentration of hypochlorous acid in the inactivating water can be adjusted to a predetermined (desired) concentration. Therefore, inactivating water containing a high concentration of hypochlorous acid can be supplied to the capture portion 72, and thus the time required to inactivate the virus or the like captured by the capture portion 72 can be shortened.

Still furthermore, the concentration of hypochlorous acid in inactivating water is adjusted by changing the flow rate of tap water passing between the electrodes 32 and 33. In place of this construction, the following construction may be adopted. That is, the stock tank (electrolytic tank) is disposed in the water supply pipe, a pair of electrodes are disposed in the stock tank, and the stock (retention) time of tap water stocked in the stock tank is changed, whereby the concentration of hypochlorous acid in the inactivating water is adjusted to a predetermined concentration.

Still furthermore, in this embodiment, the filter 82 is continuously operated. However, a sufficient amount of virus may be captured to the filter 82 by intermittently driving the driving motor 83, and then the driving motor 83 may be rotated by inactivate the virus.

Furthermore, in the above-described embodiment, the water-holding member 85 for holding inactivating water is provided to the surface of the roller 81B, and the inactivating water is supplied to the filter 82 through the water-holding member 85. However, the present invention is not limited to this embodiment. For example, a spray nozzle for spraying inactivating water along the width direction of the filter 82 may be provide so that the inactivating water is directly supplied to the filter through the spray nozzle.

Still furthermore, in the above-described embodiment, the capture portion 72 is disposed at the air blow-out port of the air conditioner main body 1. However, the present invention is not limited to this embodiment, and the capture portion 72 may be disposed at the air suction port 11. According to this construction, cleaned air is passed through the air conditioner and thus the inside of the air conditioner can be sterilized.

Still furthermore, in the above-described embodiment, the electret filter is provided to the filter 82 of the capture portion 72. However, the present invention is not limited to this embodiment, and an HEPA filter, a high-performance filter, an middle-performance filter or the like may be used.

The present invention is not limited to the above-described embodiments, and other various modifications may be made to the embodiments without departing from the subject matter of the present invention. In the above-described embodiments, the construction for generating hypochlorous acid as active oxygen specifies is adopted. However, a construction for generating ozone ($O_3$), hydrogen peroxide ($H_2O_2$) or the like as active oxygen species may be adopted. In this case, when platinum tantalum electrodes are used, active oxygen species can be generated from even water containing rare ion species stably with high efficiency by electrolysis.

At this time, at the anode electrode, the following reaction occurs:

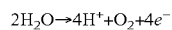

At the same time, the following reactions occur:

$$3H_2O \rightarrow O_3 + 6H^+ + 6e^-$$

$$2H_2O \rightarrow O_3 + 4H^+ + 4e^-$$

Accordingly, ozone ($O_3$) is generated. Furthermore, at the cathode electrode, $O_2^-$ generated in the electrode reaction and $H^+$ in the solution are bonded to each other like the following reactions, and hydrogen peroxide ($H_2O_2$) is generated.

$$4H^+ + 4e^- + (4OH^+) \rightarrow 2H_2 + (4OH^-)$$

$$O_2^- + e^- + 2H^+ \rightarrow H_2O_2$$

In this construction, ozone ($O_3$) or hydrogen peroxide ($H_2O_2$) which has strong sterilizing power is generated by supplying current to the electrodes, and thus humidifying water containing ozone ($O_3$) or hydrogen peroxide ($H_2O_2$) can be made. The concentration of ozone ($O_3$) or hydrogen peroxide ($H_2O_2$) in the humidifying water is adjusted to a concentration suitable to inactivate a target virus or the like, and air is passed through the humidifying element supplied with the humidifying water containing ozone ($O_3$) or hydrogen peroxide ($H_2O_2$) whose concentration is adjusted as described above, thereby inactivating target virus or the like floated in the air. Furthermore, when foul odor passes through the humidifying element, it reacts with ozone or hydrogen peroxide in the humidifying water, and it is ionized and dissolved in the humidifying water, so that the foul odor is removed from the air, thereby performing deodorization.

Furthermore, in the above-described embodiments, the humidifying water discharged from the humidifier 5 or the capture portion 72 is stocked in the drain pan 13, and then discharged to the outside of the air conditioner through the drain pump 15 together with the drain water. However, a part of the drain water or the overall drain water may be returned to the electrolytic unit and re-used. In this case, sterilized humidifying water is electrolyzed in the electrolytic unit again, and thus occurrence of various bacteria in humidifying water is prevented when it is re-used. Furthermore, by re-using humidifying water, the supply amount of tap water can be reduced, and thus energy saving can be performed.

Furthermore, when scale is deposited on the electrode (cathode) by electrolyzing tap water, the electrical conductivity is lowered and thus it is difficult to continuously carry out the electrolysis. In this case, it is effective to invert the polarities of the electrodes (the plus and minus polarities of the electrodes are switched to each other). The scale deposited on the cathode electrode can be removed by electrolyzing tap water while the cathode electrode is used as the anode electrode. In this polarity inverting control, the polarities may be regularly inverted by using a timer, or irregularly inverted like the polarities are inverted every time the operation is started. Furthermore, increase of the electrolysis resistance (reduction in electrolytic current or increase in electrolytic voltage) may be detected to invert the polarities on the basis of the detection result.

Furthermore, in the above-described embodiments, the concentration of hypochlorous acid in the humidifying water is adjusted to a predetermined concentration in accordance with the detected conductivity of tap water, however, the present invention is not limited to this embodiment. For example, the concentration of chlorine ions in tap water may be measured and the concentration of hypochlorous acid may be adjusted to a predetermined concentration in humidifying water in accordance with the measured concentration of chlorine ions. In this case, an ion concentration sensor for measuring the concentration of chlorine ions is provided to the water supply pipe 21.

Still furthermore, in the above-described embodiments, the conductivity of tap water is measured by using the conductivity meter. However, a current value when a predetermined voltage is applied to each electrode is detected, and the conductivity may be calculated from the current value. In this case, the conductivity can be detected by using existing electrodes, and thus the number of parts can be reduced, so that the cost can be reduced and the space can be reduced.

Still furthermore, in the above-described embodiments, the present invention is applied to the ceiling-suspended type air conditioner, however, the present invention is not limited to this type of air conditioner. For example, the present invention may be applied to various types of air conditioners such as a wall-hanging type air conditioner, an in-ceiling embedded (cassette) type air conditioner, etc.

Still furthermore, in the above-described embodiments, the number of the electrodes used for electrolysis is equal to two. However, the number of the electrodes is not particularly limited to two, and the number of electrodes may be equal to three or more.

What is claimed is:

1. An inactivating device for inactivating inactivation targets comprising at least one of virus and bacteria contained in air, comprising:
a humidifying unit for humidifying flowing air;
a humidifying water supply unit for supplying the humidifying unit with humidifying water containing active oxygen species having an inactivating action on the inactivation targets, the active oxygen species being achieved by electrolyzing tap water;
a selector configured to select a specific inactivation target among the inactivation targets; and
a concentration adjusting unit for adjusting the concentration of the active oxygen species in the humidifying water to a predetermined concentration with respect to the specific inactivation target,
wherein the humidifying water is tap water containing chlorine ions, and the concentration adjusting unit is equipped with a flow rate adjusting valve for adjusting the flow rate of humidifying water in accordance with the concentration of chlorine ions of tap water.

2. The inactivating device according to claim 1, wherein the humidifying water supply unit is equipped with at least a pair of electrodes for generating the humidifying water, and the concentration adjusting unit changes the flow rate of tap water passing between the electrodes so that the concentration of the active oxygen species in the humidifying water is adjusted to the predetermined concentration.

3. The inactivating device according to claim 1, wherein the concentration adjusting unit is equipped with a flow rate adjusting valve for adjusting the flow rate of humidifying water in accordance with the conductivity of tap water.

4. The inactivating device according to claim 1, wherein the humidifying water supply unit is equipped with at least a pair of electrodes for generating the humidifying water, and the concentration adjusting means varies current flowing between the electrodes or a voltage applied between the electrodes so that the concentration of the active oxygen species in the humidifying water is adjusted to the predetermined concentration.

5. The inactivating device according to claim 4, wherein the humidifying water is tap water containing chlorine ions, and the concentration adjusting means varies the current flowing between the electrodes or the voltage applied between the electrodes in accordance with the concentration of chlorine ions in the tap water.

6. The inactivating device according to claim 1, wherein the humidifying water supply unit is equipped with at least a pair of electrodes for generating the humidifying water, and the concentration adjusting unit varies a time for current supply to the electrodes so that the concentration of the active oxygen species in the humidifying water is adjusted to the predetermined concentration.

7. The inactivating device according to claim 6, wherein the humidifying water is tap water containing chlorine ions, and the concentration adjusting unit varies the time for current supply to the electrodes in accordance with the concentration of chlorine ions of the tap water.

8. The inactivating device according to claim 1, wherein the humidifying water supply unit comprises a stock tank for temporarily stocking tap water, and at least a pair of electrodes that are disposed in the stock tank and generate humidifying water, and the concentration adjusting unit varies any one of current flowing between the electrodes, a voltage applied between the electrodes and a time for current supply to the electrodes so that the concentration of the active oxygen species in the humidifying water is adjusted to the predetermined concentration.

9. The inactivating device according to claim 1, wherein the active species contain at least one of hypochlorous acid, ozone and hydrogen peroxide.

10. The inactivating device according to claim 1, wherein the polarities of the electrodes are inverted regularly or irregularly under a predetermined condition.

* * * * *